United States Patent [19]

Coates et al.

[11] 4,119,558
[45] Oct. 10, 1978

[54] LIQUID CRYSTAL MATERIALS

[75] Inventors: David Coates, Bishops Stortford; George William Gray, Cottingham, both of England

[73] Assignee: The Secretary of State for Defence in Her Britannic Majesty's Government of the United Kingdom of Great Britain and Northern Ireland, London, England

[21] Appl. No.: 821,919

[22] Filed: Aug. 4, 1977

[30] Foreign Application Priority Data

Aug. 13, 1976 [GB] United Kingdom ............... 33861/76

[51] Int. Cl.$^2$ .......................... C09K 3/34; G02F 1/13; C07C 69/76; C07C 69/78
[52] U.S. Cl. .................................... 252/299; 252/408; 350/346; 350/350; 560/65; 560/66
[58] Field of Search ............................. 252/299, 408; 350/160 LC, 350, 346; 260/473 R; 560/65, 66

[56] References Cited

U.S. PATENT DOCUMENTS

| 3,915,883 | 10/1975 | Van Meter et al. | 252/299 |
| 3,925,237 | 12/1975 | Ross et al. | 252/299 |
| 3,947,375 | 3/1976 | Gray et al. | 252/299 |
| 4,009,934 | 3/1977 | Goodwin et al. | 350/160 LC |

FOREIGN PATENT DOCUMENTS 2,538,865  3/1976  Fed. Rep. of Germany ........... 252/299

OTHER PUBLICATIONS

Gray, G. W., et al., Liquid Crystals & Plastic Crystals, vol. 1, John Wiley & Sons, Inc., N. Y., pp. 103-152, pp. 136-137 (1974).

Primary Examiner—Benjamin R. Padgett
Assistant Examiner—T. S. Gron
Attorney, Agent, or Firm—Stevens, Davis, Miller & Mosher

[57] ABSTRACT

Novel liquid crystal materials are provided having the general formula

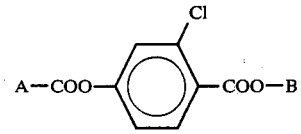

where A is a 4-alkylphenyl group and B is a 2-(6-alkyl)-naphthyl group, or vice versa, wherein the alkyl groups in A and B may be the same or different. These materials have a dielectric anisotropy sign change at moderate frequencies, i.e., in the range 1kHz to 50kHz and are thus useful for twisted nematic device cells of the frequency switching type.

21 Claims, 1 Drawing Figure

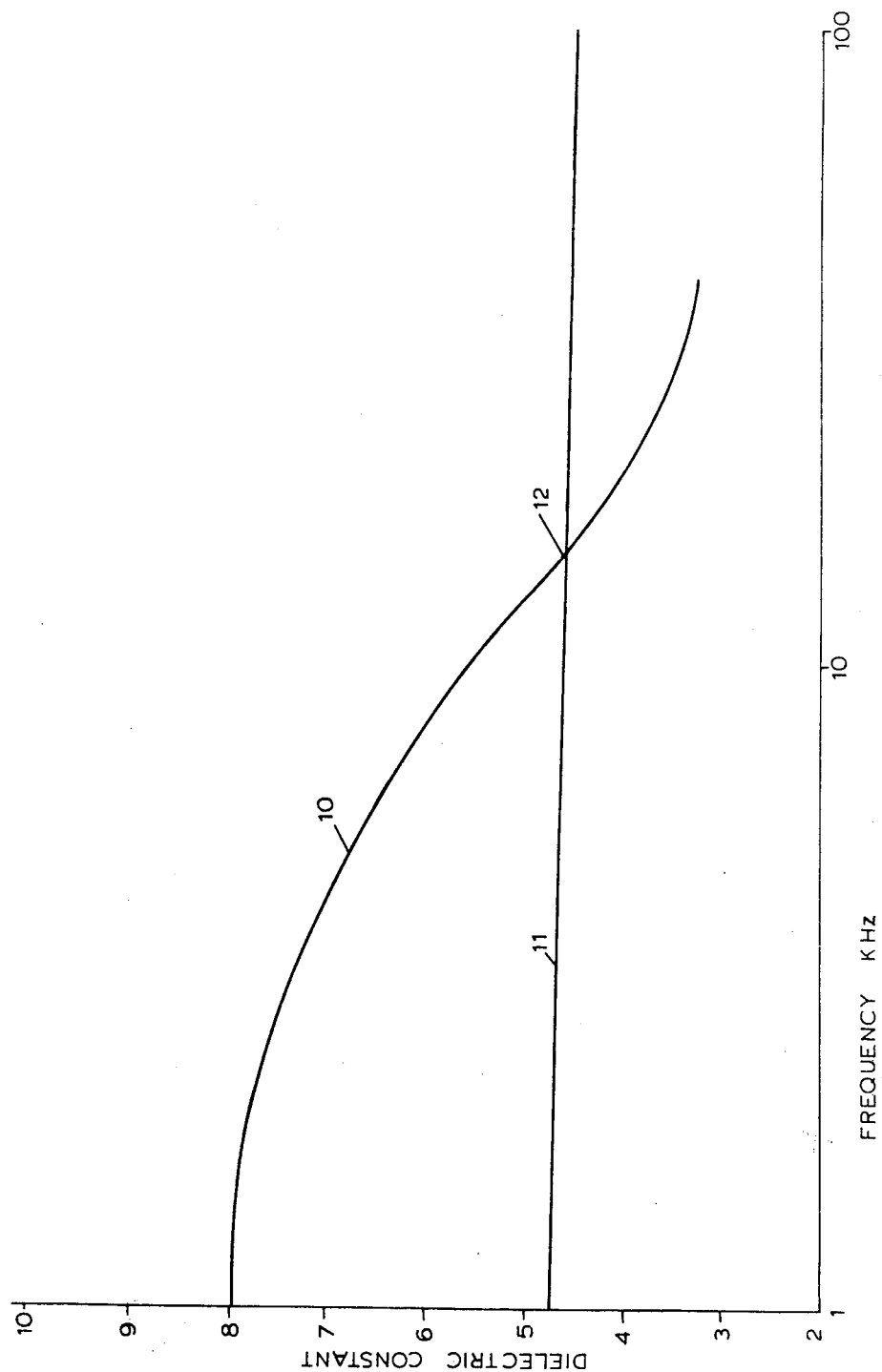

LIQUID CRYSTAL MATERIALS

The present invention is concerned with aromatic diesters that display liquid crystalline properties.

Liquid crystal phases are exhibited by certain organic compounds and constitute an intermediate phase which exists between the crystalline solid and the fully disordered liquid phase and within which certain long range ordering of the molecules takes place.

There are two broad types of liquid crystal phase; the smectic mesophase in which the long range ordering is of a substantially lamellar type and the nematic mesophase in which the ordering is substantially linear, ie the molecules tend to line up with the long axes of the molecules parallel. Included sometimes as a sub-class of the nematic mesophase and sometimes classified as a separate mesophase is the cholesteric mesophase. This last type has a helical short-range order superimposed upon the linear order of the nematic mesophase. The possession of liquid crystal properties generally arises with elongated molecules.

The dielectric constants of elongated molecules such as those of the present invention generally vary with the orientation of the molecules, and when the dielectric constant measured along the longitudinal axis of the molecule is greater than the transverse dielectric constant then the material is said to possess positive dielectric anisotropy and if the converse is true the material has negative dielectric anisotropy. It is the possession of this property of dielectric anisotropy that enables the molecules to be aligned by application of an electric field and permits the production of electro-optic display devices, for example, twisted nematic display devices and phase change devices.

In a common type of twisted nematic device cell the molecules are aligned by the application of an alternating electric field across a thin film of liquid crystal material by means of appropriately shaped electrodes when in the "on" position. The current is switched off for the "off" position and thermal movement is relied upon to provide the reorientation necessary to change the display. This is relatively unsatisfactory as it leads to twisted nematic devices having slow switching times.

In general the dielectric anisotropy of most liquid crystal materials is dependent upon the frequency of the applied alternating electric field and a change from positive to negative dielectric anisotropy takes place at a sufficiently high frequency. This gives the possibility of fast switching triggered by changing the frequency of the applied alternating electric field. Unfortunately in general this change over takes place at frequencies that are too high for use in a practical device cell, for example at frequencies of greater than 1 MHz.

It is an object of the present invention to provide a class of liquid crystal materials having a reversal of dielectric anisotropy at a frequency attainable in a practical device cell.

In accordance with the present invention a liquid crystal material is an aromatic diester having the formula:

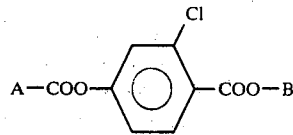

in which A is a 4-alkylphenyl group and B is a 2-(6-alkyl)-naphthyl group or A is a 2-(6-alkyl)-naphthyl group and B is a 4-alkylphenyl group, the alkyl groups may be the same or different. Advantageously the alkyl groups are straight chain alkyl groups having up to ten and preferably four to ten carbon atoms.

The aromatic diesters of the present invention have a positive dielectric anisotropy when in an alternating electric field of low frequency and the sign of dielectric anisotropy changes at moderate frequencies.

It will of course be clear to those skilled in the art that the frequencies used in a practical device cannot be too close to the frequency at which the dielectric anisotropy changes from positive to negative but aromatic diesters of the present invention have positive dielectric anisotropy at frequencies below about 1kHz and negative dielectric anisotropy above about 50kHz, the switch over taking place within that range, which for the purpose of the present specification is moderate frequency.

In accordance with an important aspect the present invention a twisted nematic electro-optic device cell of the frequency switching type includes as its liquid crystal material an aromatic diester as defined above or a mixture (solution) of such aromatic diesters with one another or with other liquid crystal materials. It is necessary that liquid crystal materials mixed with aromatic diesters of the present invention for use in a twisted nematic device of the frequency switching type should have switching characteristics compatible with those of the aromatic diester of the present invention.

Aromatic diesters of the present invention may be used alone or in mixture (solution) with themselves or with other liquid crystal materials in twisted nematic device cells or phase change device cells, which do not use frequency dependence of dielectric anisotropy for switching, and in accordance with a further aspect of the present invention a twisted nematic cell or a phase change cell incorporates an aromatic diester as defined immediately above in conjunction with a low melting nematogen for example 4-n-heptyl-4-cyanobiphenyl or other members of that class of cyanobiphenyl. Furthermore a phase change cell may incorporate an aromatic diester as defined above in conjunction with a cholesterogen.

The present invention will now be described, by way of example only, with reference to the following Examples, which illustrate methods of prearation and properties of compounds of the present invention and with reference to the accompanying drawings, which are graphs illustrating the dependence of dielectric anisotropy upon frequency of applied field.

In the following specific description the following symbols indicating phases are used:

C — Crystal
$S_A$ — Smectic A
N — Nematic
I — Isotropic liquid
( ) — brackets around a temperature indicate a monotropic transition which is not observed during a heating cycle, but which may be observed on cooling.

Phase changes are indicated thus:

C-N — indicates the change from crystal to nematic liquid crystal phase. Temperatures are given in °C.

The liquid crystal materials are diesters prepared by two successive esterification reactions in which 2-chloro-4-hydroxybenzoic acid (formula I in the general synthetic scheme below) is esterified with a 4-alkyl-phenol (II) or a 6-alkyl-2-naphthol (III) to yield hydroxyester products (IV) or (V) respectively. These hydroxyesters are further esterified with a 6-alkyl-2-naphthoic acid (VI) or a 4-alkyl-benzoic acid (VII) to yield respectively diesters (VIII) or (IX).

6-alkyl-2-naphthols are required together with 2-chloro-4-hydroxybenzoic acid in order to synthesise the desired diesters in accordance with the scheme.

PREPARATION AND AVAILABILITY OF REQUIRED SUBSTITUTED PHENOLS AND NAPHTHOLS

4-Alkylphenols (II) are either commercially available or can be prepared by the standard method described by Van der Veen, de Jeu, Grobben and Boven (Mol. Cryst. Liq. Cryst., 1972, 17, 291) for the preparation of 4-alkylanilines, followed by diazotization of the amines and hydrolysis of the diazonium sulphates.

6-Alkyl-2-naphthols (III) may be prepared as de-

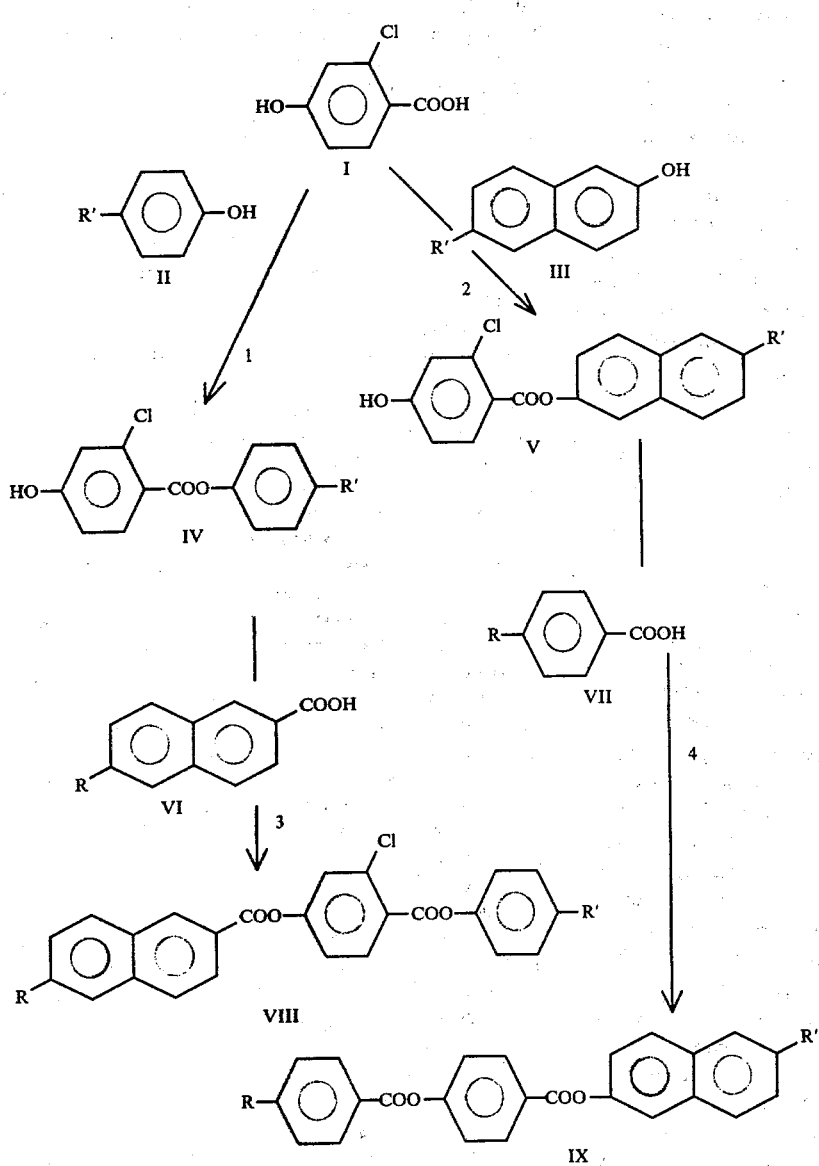

It will be apparent that a variety of 4-alkyl-benzoic acids 6-alkyl-2-naphthoic acids, 4-alkyl-phenols and scribed in Example 1 by the following route:

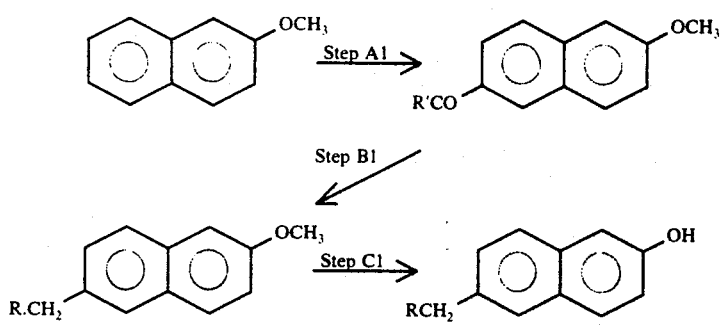

where R is an alkyl group, for example a n-alkyl group.

EXAMPLE 1

Step A1: The production of 6-alkanoyl-2-methoxynaphthalenes (by Friedel-Crafts Acylation).

Commercially available 2-methoxynaphthalene (25.8g; 0.15 mole) is added to a cold solution of anhydrous aluminium trichloride (22g; 0.17 mole) in dry nitrobenzene (120 ml). The appropriate alkanoyl chloride (RCOCl) (0.17 mole) is added dropwise to the stirred mixture which, when addition is complete, is allowed to stand at room temperature for 48hr. The dark mixture is then poured onto a mixture of ice, water and concentrated hydrochloric acid and stirred for 0.5hr. The nitrobenzene layer is separated off and dried over anhydrous magnesium sulphate. The mixture is then distilled under reduced pressure, initially boiling off the nitrobenzene; the required product then distils at about 180°–200° C. at 1mm Hg pressure. The products usually solidify on cooling.

Step B1: 6-Alkyl-2-methoxynaphthalenes may be produced by the standard synthetic method described by Albrecht, Gustafson and Horgan (J Org Chem, 1972, 37, 3355).

Step C1: The production of 6-alkyl-2-naphthols.

A mixture of 6-alkyl-2-methoxynaphthalene (6.5g) in a mixture of constant boiling 46% aqueous hydrobromic acid (24ml) and a 45% solution of hydrogen bromide in glacial acetic acid (39ml) is heated under reflux for 24hr. The solution is cooled, poured into a large volume of water, and the 6-alkyl-2-naphthol which precipitates is filtered at the pump. The product is dried and crystallised from a suitable solvent, eg aqueous ethanol.

PREPARATION AND AVAILABILITY OF THE REQUIRED SUBSTITUTED BENZOIC AND NAPHTHOIC ACIDS

2-Chloro-4-hydroxybenzoic acid (I) is a commercially available material and 4-alkylbenzoic acids (VII) are either commercially available or can be prepared by the standard synthetic method of the acetylation of commercially available alkylbenzenes (Friedel-Crafts Acylation) followed by hypobromite oxidation of the 4-alkylacetophenone to the corresponding acid as described by Gray and Brynmor Jones, J. Chem. Soc., 1954, 678.

6-Alkyl-2-naphthoic acids (VI) may be prepared by the following route:

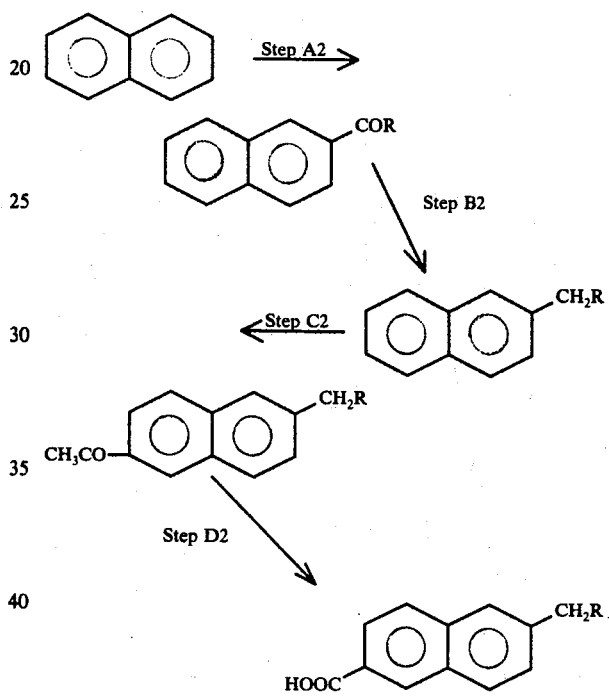

where R is an alkyl group, for example a n-alkyl group as described in Example 2.

EXAMPLE 2

Step A2: The production of 2-alkanoylnaphthalenes (by Friedel-Crafts Acylation)

Commercially available naphthalene (0.3 mole) is mixed with dry nitrobenzene (155ml) and cooled to about 0° C. The appropriate alkanoyl chloride (RCOCl) (0.33 mole) is added and the mixture stirred. Aluminium trichloride (anhydrous) (0.35 mole) is gradually added to the cooled, stirred mixture over about 2hr. Calcium chloride guard tubes protect the reactants from atmospheric moisture. The mixture is left to stand in a refrigerator overnight. The dark mixture is poured onto ice, water and concentrated hydrochloric acid and stirred (30 min). The nitrobenzene layer is separated, dried and the solvent distilled under reduced pressure. The residue of the required product boils at about 170°–180° C. at 4mm Hg pressure. The products usually solidify on cooling.

Step B2: The reduction of the product of Step A2 to 2-alkylnaphthalenes may be carried out by the standard method described by Albrecht, Gustafson and Horgan (J Org Chem., 1972, 37, 3355).

Step C2: The production of 6-acetyl-2-alkylnaphthalenes (by Friedel-Crafts Acylation).

Anhydrous aluminium trichloride (0.053 mole) is dissolved in dry nitrobenzene (50 ml) and cooled in an ice bath; the 2-alkyl-naphthalene (0.048 mole) is then added. Acetyl chloride (0.05 mole) is added dropwise to the stirred and cooled solution. The reactants are protected from atmospheric moisture by calcium chloride guard tubes. After the mixture has stood at room temperature for 40–48 hr, it is poured onto a mixture of ice, water and concentrated hydrochloric acid and stirred (30 min.). The nitrobenzene layer is separated off, dried and the solvent distilled off under reduced pressure. The required product boils at about 160° C. at 0.2mm Hg pressure and consists of two isomers from which pure 6-acetyl-2-alkylnaphthalene is separated by column chromatography on silica gel using a chloroform/hexane mixture as eluent.

Step D2: The oxidation of the products of Step C2 to 6-alkyl-2-naphthoic acids by the haloform reaction may be carried out by the standard method for oxidation of aryl methyl ketones to aromatic acids described by Gray and Brynmor Jones (J Chem Soc., 1954, 678). After treatment of the methyl ketone with an alkaline solution of sodium hypobromite at 35°–40° C., the aromatic acid is obtained by acidification and filtration.

The products are crystallised from solvents such as ethanol or glacial acetic acid.

PREPARATION OF HYDROXYESTER IV & DIESTER VIII EXEMPLIFYING REACTIONS 1 AND 3 FROM THE GENERAL SCHEME ABOVE

A representative preparative technique is described in each step of the following examples. In each step, the substituted phenol or carboxylic acid chosen for exemplification could be replaced by any of the phenols (or 2-naphthols) or carboxylic acids previously disclosed.

EXAMPLE 3

The production of 4-n-pentyl-2-chloro-4-hydroxybenzoate (IV,R'=4-n-pentyl) exemplifying reaction 1 of the general synthetic scheme.

This esterification may be carried out by the method described by Lowrance (Tetrahedron Lett., 1971,3453). The reactants (2-chloro-4-hydroxybenzoic acid and 4-n-pentylphenol in equimolar amounts) are dissolved in toluene and heated in a Dean and Stark apparatus together with sulphuric acid and boric acid as catalysts. After crystallisation from ethanol, the mp of the product is 150°–151° C.

EXAMPLE 4

The production of 4-n-pentylphenyl 2-chloro-4-(6'-n-pentyl-2'-naphthoyloxy)benzoate (VIII, R=n-pentyl, R'=n-pentyl), exemplifying reaction 3 of the general synthetic scheme above.

6-n-Pentyl-2-naphthoic acid (0.01 mole) is converted into the acid chloride by standard techniques using thionyl chloride. After removal of excess of thionyl chloride by distillation, the residual acid chloride is mixed with dry pyridine (40 ml) and cooled to 0°–5° C. The product from Example 3 (0.014 mole) is then added and the solution stirred at room temperature for 20 hr; the reaction mixture is protected from atmospheric moisture during this time using a calcium chloride guard tube. The mixture is then rotary evaporated to remove pyridine; the residual ester is purified by column chromatography on silica gel using chloroform or a chloroform; hexane (2:1) mixture as eluent. The pure di-ester VIII is isolated and crystallised from hexane or methanol until constant transition temperatures are obtained — crystal — nematic phase (C-N), 63.8° C.; nematic phase-isotropic liquid (N-I), 190.4° C.

By techniques analogous to those described above a series of diesters were prepared and their physical properties are given in Tables 1 and 2 below.

TABLE 1

| | | Transition Temperatures ° C | | |
|---|---|---|---|---|
| NO | R | R¹ | C-N(or$S_A$) | $S_A$-N | N-I |
| 1 | n-C$_4$H$_9$ | n-C$_5$H$_{11}$ | 74.5 | — | 109.4 |
| 2 | n-C$_4$H$_9$ | n-C$_6$H$_{13}$ | 71.1 | — | 181.0 |
| 3 | n-C$_5$H$_{11}$ | n-C$_4$H$_9$ | 88.3 | — | 189.0 |
| 4 | n-C$_5$H$_{11}$ | n-C$_5$H$_{11}$ | 63.8 | — | 190.4 |
| 5 | n-C$_5$H$_{11}$ | n-C$_6$H$_{13}$ | 63.7 | — | 182.8 |
| 6 | n-C$_6$H$_{13}$ | n-C$_4$H$_9$ | 74.2 | (66.0) | 179.9 |
| 7 | n-C$_6$H$_{13}$ | n-C$_5$H$_{11}$ | 68.6 | (52.5) | 178.9 |
| 8 | n-C$_6$H$_{13}$ | n-C$_6$H$_{13}$ | 55.0 | 80.4 | 171.0 |
| 9 | n-C$_7$H$_{15}$ | n-C$_4$H$_9$ | 70.5 | 93.3 | 178.5 |
| 10 | n-C$_7$H$_{15}$ | n-C$_5$H$_{11}$ | 52.2 | 95.6 | 176.7 |

TABLE 2

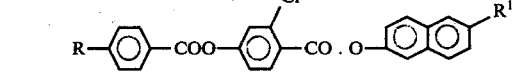

where R is n-C$_5$H$_{11}$ and R' is n-C$_5$H$_{11}$, C-N, 94.8° C. and N-I 193.7° C.

The variation of dielectric constant with frequency was determined for a sample of compound 4 of Table 1 of high purity using a liquid crystal cell 1cm square and 50 μm thick. A magnetic field of strength 9.7kOe was used to align the liquid crystal materials in the two required orientations. The measurements were carried out at 66° C.

In the accompanying FIG., 10 represents the change of $\epsilon_{\parallel}$, which is the dielectric constant measured parallel to the long axis of the molecule, and 11 represents the change of $\epsilon_{\perp}$, which is the dielectric constant measured perpendicular to the long axis of the molecule. The cross-over frequency, $F_c$, at which $\epsilon_{\parallel}$ and $\epsilon_{\perp}$ have the same value is indicated by 12 and occurs at 15kHz. This material is useful in a device having a low frequency drive of 500Hz and a high frequency drive of 100kHz.

The aromatic diesters of the present invention have lower melting points and wider nematic ranges when mixed, in eutectic proportions, with one another and with other liquid crystal materials.

Five mixtures are listed below in Table 3 with their physical properties, the diesters of the present invention being designated by the number given them in Table 1 above while mixtures D & E contain 4-n-pentyl-4'-cyanobiphenyl designated 5CB in Table 3 below and 4-n-hexyl-4'-cyanobiphenyl designated 6CB.

TABLE 3
EXAMPLES OF EUTECTIC MIXTURE COMPOSITIONS AND THEIR TRANSITION TEMPERATURES

| | Components | Mole fraction | C-N(° C) | N-I(° C) |
|---|---|---|---|---|
| MIXTURE A | 4-(Table 1) | 0.42 | | |
| | 7-(Table 1) | 0.15 | 30.1 | 179.4 |
| | 8-(Table 1) | 0.43 | | |
| MIXTURE B | 4-(Table 1) | 0.66 | 44.6 | 187.6 |
| | 7-(Table 1) | 0.34 | | |
| MIXTURE C | 4-(Table 1) | 0.48 | 34.3 | 179.1 |
| | 7-(Table 1) | 0.52 | | |
| MIXTURE D | 4-(Table 1) | 0.11 | | |
| | 5CB | 0.44 | −7.5 | 49.2 |
| | 6CB | 0.45 | | |
| MIXTURE E | 4-(Table 1) | 0.11 | | |
| | 8-(Table 1) | 0.05 | −8.8 | 46.0 |
| | 5CB | 0.41 | | |
| | 6CB | 0.43 | | |

These mixtures, and many others of which they are typical examples, provide colourless, stable nematic liquid crystal phases with thermal properties which are suitable for their use as liquid crystal materials for electro-optical display devices of various kinds, but it will be realised that the switching properties of the alkylcyanobiphenyls differ from the aromatic diesters of the present invention to such an extent that such mixtures cannot be used in a twisted nematic device of the frequency switching type.

We claim:

1. A liquid crystal material which is an aromatic diester having the formula.

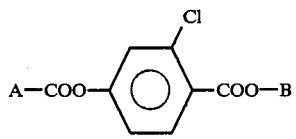

in which A is a 4-alkylphenyl group and B is a 2-(6-alkyl)naphthyl group or A is a 2-(6-alkyl)naphthyl group and B is a 4-alkylphenyl group wherein the alkyl groups may be the same or different.

2. A liquid crystal material as claimed in claim 1 and wherein the alkyl groups are straight chain alkyl groups having up to ten carbon atoms.

3. A liquid crystal material as claimed in claim 1 and wherein the alkyl groups are straight chain alkyl groups having from four to ten carbon atoms.

4. A liquid crystal material as claimed in claim 1 and having a dielectric anisotropy sign reversal in the frequency range 1kHz to 50kHz.

5. A liquid crystal material which is a diester having the formula:

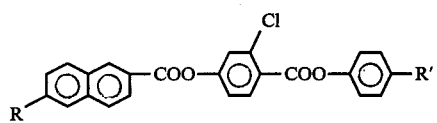

and wherein R and R', which may be the same or different are straight chain alkyl groups having four to seven carbon atoms inclusive.

6. A liquid crystal material as claimed in claim 4 and wherein R is n-butyl and R' is n-pentyl.

7. A liquid crystal material as claimed in claim 4 and wherein R is n-butyl and R' is n-hexyl.

8. A liquid crystal material as claimed in claim 4 and wherein R is n-pentyl and R' is n-butyl.

9. A liquid crystal material as claimed in claim 4 and wherein R is n-pentyl and R' is n-pentyl.

10. A liquid crystal material as claimed in claim 4 and wherein R is n-pentyl and R' is n-hexyl.

11. A liquid crystal material as claimed in claim 4 and wherein R is n-hexyl and R' is n-butyl.

12. A liquid crystal material as claimed in claim 4 and wherein R is n-hexyl and R' is n-pentyl.

13. A liquid crystal material as claimed in claim 4 and wherein R is n-hexyl and R' is n-hexyl.

14. A liquid crystal material as claimed in claim 4 and wherein R is n-heptyl and R' is n-butyl.

15. A liquid crystal material as claimed in claim 4 and wherein R is N-heptyl and R' is n-pentyl.

16. A liquid crystal material which is an aromatic diester having the formula:

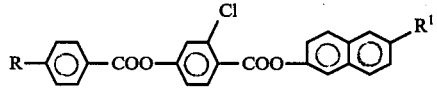

and wherein R and R' are both n-pentyl.

17. A twisted nematic electro-optic display device cell of the frequency switching type wherein the liquid crystal material is a material as claimed in claim 1 or mixtures thereof.

18. A device cell as claimed in claim 17 and wherein the frequencies employed in the cell are either below 1kHz or above 50kHz, the lower driving frequency being below 1kHz and the higher driving frequency above 50kHz.

19. An electro-optic display device cell of the twisted nematic type other than a frequency switching device and which includes as its liquid crystal material a material as claimed in claim 1, or a mixture or solution of such materials with a low melting nematogen which is a 4-alkyl-4'-cyanobiphenyl.

20. A device cell as claimed in claim 19 and wherein the mixture is an eutectic mixture.

21. A device cell as claimed in claim 19 and wherein the nematogen is 4-n-heptyl-4'-cyanobiphenyl.

* * * * *